United States Patent
Tinti et al.

(10) Patent No.: US 9,278,065 B2
(45) Date of Patent: Mar. 8, 2016

(54) DELIVERY SYSTEMS FOR SOLUBILISING WATER-INSOLUBLE PHARMACEUTICAL ACTIVE INGREDIENTS

(75) Inventors: Flavia Giuliana Tinti, Campinas (BR); Marcia Cristina Breitkreitz, Campinas (BR); Vladimir Matha, Borsov nad Vitavou (CZ); Carlo Oliani, Cinisello Balsamo Milano (IT)

(73) Assignee: EMS S/A, HORTOLANDIA (BR)

( * ) Notice: Subject to any disclaimer, the term of this patent is extended or adjusted under 35 U.S.C. 154(b) by 878 days.

(21) Appl. No.: 12/672,574

(22) PCT Filed: Aug. 11, 2008
(Under 37 CFR 1.47)

(86) PCT No.: PCT/IB2008/002552
§ 371 (c)(1),
(2), (4) Date: Mar. 2, 2011

(87) PCT Pub. No.: WO2009/019604
PCT Pub. Date: Feb. 12, 2009

(65) Prior Publication Data
US 2012/0177692 A1      Jul. 12, 2012

(30) Foreign Application Priority Data
Aug. 9, 2007   (GB) .................................. 0715493.3

(51) Int. Cl.
A61K 9/107     (2006.01)
A61K 9/48      (2006.01)
A61K 31/07     (2006.01)

(52) U.S. Cl.
CPC ............. *A61K 9/1075* (2013.01); *A61K 9/4866* (2013.01); *A61K 31/07* (2013.01)

(58) Field of Classification Search
None
See application file for complete search history.

(56) References Cited

U.S. PATENT DOCUMENTS

| | | | |
|---|---|---|---|
| 4,388,307 A | 6/1983 | Cavanak | |
| 4,990,337 A | 2/1991 | Kurihara et al. | |
| 5,047,396 A | 9/1991 | Orbán et al. | |
| 5,342,625 A | 8/1994 | Hauer et al. | |
| 5,589,455 A | 12/1996 | Woo | |
| 5,639,724 A | 6/1997 | Cavanak | |
| 5,756,450 A | 5/1998 | Hahn et al. | |
| 6,258,808 B1 | 7/2001 | Hauer et al. | |
| 6,267,985 B1* | 7/2001 | Chen et al. | 424/451 |
| 6,420,355 B2 | 7/2002 | Richter et al. | |
| 6,702,995 B1* | 3/2004 | Johnstone et al. | 424/1.65 |
| 7,026,290 B1* | 4/2006 | Domb | 424/451 |
| 2002/0012680 A1* | 1/2002 | Patel et al. | 424/400 |
| 2002/0107183 A1 | 8/2002 | Petszulat et al. | |
| 2002/0120015 A1 | 8/2002 | Dennis et al. | |
| 2006/0094692 A1 | 5/2006 | Hausheer et al. | |
| 2009/0062397 A1* | 3/2009 | Tongiani et al. | 514/628 |

FOREIGN PATENT DOCUMENTS

| | | |
|---|---|---|
| DE | 4418115 A1 | 12/1994 |
| DE | 4418155 A1 | 12/1994 |
| EP | 0793966 A1 | 9/1997 |
| GB | 2222770 A | 3/1990 |
| GB | 2222770 B | 3/1990 |
| GB | 2228198 A | 8/1990 |
| WO | 96/03113 A1 | 2/1996 |
| WO | 00/03753 A2 | 1/2000 |
| WO | 00/37050 A1 | 6/2000 |
| WO | 01/01960 A1 | 1/2001 |
| WO | 02/45696 A1 | 6/2002 |
| WO | 03/055466 A1 | 7/2003 |
| WO | WO 03/055466 * | 7/2003 |
| WO | 2004/009121 A1 | 1/2004 |
| WO | 2004/014341 A1 | 2/2004 |
| WO | WO 2004/014341 * | 2/2004 |
| WO | 2004/043445 A1 | 5/2004 |
| WO | 2004/093915 A1 | 11/2004 |

OTHER PUBLICATIONS

International Search Report (PCT/IB2008/002552, published as WO2009/019604), mailed Jun. 5, 2009.
German Search Report (GB0715493.3) Dated: Dec. 6, 2007.

* cited by examiner

*Primary Examiner* — Johann R Richter
*Assistant Examiner* — Katherine Peebles
(74) *Attorney, Agent, or Firm* — The Dobrusin Law Firm, P.C.

(57) ABSTRACT

A delivery system for water-insoluble pharmaceutical active ingredients is provided. The delivery system includes water-insoluble pharmaceutical active ingredient(s), organic solvent(s) and amphiphilic co-solvent(s), and a mixture of hydrophilic and hydrophobic non-ionic surfactants. Upon dilution in an aqueous medium, this formulation forms spontaneously dispersion of non-ionic surfactant nanoparticles.

20 Claims, No Drawings

DELIVERY SYSTEMS FOR SOLUBILISING WATER-INSOLUBLE PHARMACEUTICAL ACTIVE INGREDIENTS

CLAIM OF BENEFIT OF FILING DATE

The present application claims the benefit of the filing date of PCT Application Serial No. PCT/IB2008/002552 (filed Aug. 11, 2008) (Published as WO 2009/019604) and GB 0715493.3 (filed Aug. 9, 2007), the contents of which are hereby incorporated by reference in their entirety.

The invention relates to drug delivery systems containing water-insoluble active pharmaceutical ingredients. More particularly, the present invention relates to oral pharmaceutical dosage forms as liquids or capsules. When administered orally, they form stable dispersion of non-ionic surfactant nanoparticles in contact with gastric fluids. In a preferred embodiment the compositions are substantially free of triacylglycerides.

A difficulty in formulating pharmaceutical active ingredients is that many of them are insoluble in water. For instance, over one third of drugs are either water-insoluble. The consequence of this is that oral formulations of water-insoluble drugs or compounds with biological uses frequently show poor and erratic bioavailability. Furthermore, water-insolubility problems can delay or completely block the development of many new drugs and other biologically useful compounds. The difficulties in water solubility can also prevent or inhibit the reformulation of certain currently marketed drugs.

Solubilisation of hydrophobic therapeutic agents in oils (triacylglycerides) represent the most common and convenient way to formulate water-insoluble compounds in pharmaceutical compositions acceptable for oral and parenteral delivery. Although the triacylglyceride-based formulations are useful in solubilising and delivering some water-insoluble pharmaceutical active ingredients, these compositions are subject to a number of significant limitations and disadvantages.

For instance U.S. Pat. No. 4,388,307 describes water-insoluble monocyclic peptide (such as cyclosporins) based compositions containing (a) a non-ionic ester of natural or hydrogenated vegetable oil a triglyceride and a polyalkylene polyol, (b) a saturated fatty acid triglyceride, and (c) a mono- or di-glyceride. These compositions are said to have improved blood level of active ingredient or avoid instability.

Although, in these systems, the emulsion particles can transport the water-insoluble active ingredient through the aqueous environment of the GIT (gastro-intestinal tract), to release the active ingredient to be absorbed through the intestinal mucosa, the triacylglyceride carrier has to be digested. In this digestion the triacylglyceride is first emulsified by bile salts followed by lipases hydrolysis (lipolysis). The rate and extent of lipolysis are dependent on several factors and are difficult to be adequately controlled. U.S. Pat. No. 4,990,337 relates to a pharmaceutical composition comprising cyclosporin in a mixture with a monoglyceride or diglyceride of a $C_6$-$C_{10}$ fatty acid in an amount sufficient to dissolve the active ingredient.

U.S. Pat. No. 5,047,396 discloses an intravenous pharmaceutical formulation composed of a) 1 part by mass of one or more cyclosporins, b) 8 to 13 parts by mass of a monoester of a saturated hydroxylated fatty acid formed with polyethylene glycol or the mixture of said monoesters, c) 4 to 10 parts by mass of one or more intravenously administrable mono- or polivalent alcohols.

A disadvantage of these formulations is that the monocytic peptides tend to agglomerate and phase-separate creating problems of storage and handling, tending to increased particle size of the emulsion generated in the GIT (gastro-intestinal tract) which slows down the rate of transport through the mucosa, hence lowering the rate and extent-of absorption of the active ingredient. Moreover, the reduction in particle size of the emulsion is also believed to render the absorption more sensitive to and dependent upon specific gastrointestinal conditions at the time of each administration, such as pH, enzyme activity, bile components, and alimentary contents. A further significant disadvantage of the triacylglyceride-containing emulsions is the dependence of active ingredient absorption on the rate and extent of lipolysis.

In order to avoid these disadvantages, and in order to obtain less variable plasma levels of the drug, oral formulations that are based on pre-concentrates of microemulsions were developed and these pre-concentrates demonstrated less individual variability, these compositions are however difficult to produce. Other compositions that are difficult to produce and just as complex, were also proposed. One formulation, (in the form of a pre-concentrate for a microemulsion) was introduced onto the market (NEORAL®) as an improvement over the previous oily solution of cyclosporin in ethanol (SAND-IMMUN®) based upon a claim that smaller particles were generated when reaching gastric fluids.

Examples of other formulations that have been proposed are as follows:

U.S. Pat. No. 5,342,625, which relates to NEORAL®, describes a composition which is said to allow a more homogeneous absorption of the active ingredient by means of a formulation which consists of a preconcentrate for microemulsion, that does not contain alkanols.

U.S. Pat. No. 5,589,455 discloses a microemulsion free from ethanol and containing (1) cyclosporin as the active ingredient; (2) polyethylene glycol having a molecular weight from 200 to 600 Daltons as cosurfactant; (3) a mixture comprising the esterification product of a fatty acid and a primary alcohol, the triglyceride of a medium-chain fatty acid and the monoglyceride of a fatty acid; and (4) a surfactant having an HLB value from 10 to 17.

U.S. Pat. No. 5,756,450 discloses a combination of cyclosporin and a water-soluble monoester of a saturated or unsaturated fatty acid and a polyol, especially a saccharide. U.S. Pat. No. 5,639,724 discloses pharmaceutical compositions comprising a cyclosporin as active ingredient, a fatty acid triglyceride, a glycerol fatty acid partial ester or propylene glycol or sorbitol complete or partial ester, preferably, and a tenside having an HLB of at least 10, without ethanol.

German Patent Application DE-4418115 discloses an at least ternary vehicle formed by the transesterification product of a vegetable oil and mono-, di- or triglyceride of oleic acid and/or linoleic acid, and/or of polyoxyethylenated vegetable oil, propylene glycol and ethanol. U.S. Pat. No. 6,258,808 describes a composition containing cyclosporin, 1,2-propylene glycol, a mixed mono-, di- and tri-glyceride and a hydrophilic surfactant.

U.S. Pat. No. 6,420,355 discloses a pharmaceutical composition in the form of an emulsion preconcentrate for oral administration and containing cyclosporin. The pharmaceutical composition has a carrier medium for cyclosporin that contains a hydrophilic organic solvent; a mixed mono-, di-, and tri-glyceride or a transesterified and polyethoxylated vegetable oil; and a polyoxyethylene-sorbitan-fatty acid ester surfactant.

Pharmaceutical compositions containing water-insoluble active ingredients are also disclosed in United States Patent Application No. US2002120015, WO02/45696, WO00/37050, WO96/03113 and WO00/03753.

United States Patent Application No. US2002/0107183A1 describes a pharmaceutical composition containing (a) cyclosporin as the active ingredient, (b) an alkylene polyether and/or an alkylene polyester as vehicles, in which the HLB of component (b) is at least 10.

In a first embodiment this invention relates to dispersion of non-Ionic surfactant nanoparticles. More particularly, but not exclusively, the invention relates to mixed non-ionic surfactant nanoparticles. In a further embodiment the invention relates to the use of the non-ionic surfactant nanoparticle for solubilising water-insoluble active pharmaceutical ingredients.

Within this application "water-insoluble" active pharmaceutical ingredient means compounds having a water solubility of less than 30 mg/ml at 20° C., corresponding to "sparingly" and less soluble compound, according to USP-26 NF21, 2003.

Formulations of water-insoluble active ingredients are normally prepared as concentrated products which are then diluted in water prior to their application. In this invention the preferred embodiment is a formulation which comprises: water-insoluble compounds diluted in the organic solvent(s) and co-solvent(s), and a non-ionic surfactant mixture. According to another aspect of this invention there is provided a method of solubilising a water-insoluble active pharmaceutical ingredient(s) by mixing it with organic solvent(s), an amphiphilic co-solvent(s) and a non-ionic surfactant mixture to provide a formulation which after diluting in aqueous media provide a surfactant nanoparticles in which the water-active pharmaceutical ingredient is solubilised therein.

The present invention therefore provides a composition for delivery of a water-insoluble active pharmaceutical ingredient(s) comprising:
i) water miscible solvent(s) which comprises ethanol and/or propyleneglycol and/or polyethoxylated;
ii) amphiphilic co-solvent(s) which comprises diethylenglycol monoethylether and/or 1,3-dimethylisosorbide and/or N-methyl-2-pyrrolidone;
iii) mixture of non-ionic at least one hydrophilic and at least one hydrophobic surfactants.

The invention further provides a method of delivering a drug to a host comprising administering the drug delivery system previously described to the host.

In yet a further embodiment the invention provides a process for the preparation of a drug delivery system comprising
a) providing a drug solution comprising a water-insoluble drug and a water-miscible organic solvent for said water-insoluble drug and an amphiphilic co-solvent;
b) providing a surfactant composition comprising at least one non-ionic hydrophilic surfactant and at least one non-ionic hydrophobic surfactant; and
c) combining said drug solution and said surfactant system to provide a drug delivery system.

In a preferred embodiment of the present invention the delivery system is substantially free of triacylglycerides.

The invention therefore provides a method for the delivery of water-insoluble active pharmaceutical ingredient materials comprising dissolving the water-insoluble ingredient in organic solvent(s) which have acceptable water affinity (e.g.: ethanol or glycols) and an amphiphilic co-solvent(s) (e.g.: diethylenglycol ethylether, DEGEE) to solubilize the water-insoluble material. Hydrophilic and hydrophobic surfactants are heated, if necessary, and mixed to make a homogenous surfactant mixture, this homogenous mixture is then mixed with the solution of the water-insoluble active pharmaceutical ingredient to provide a formulation which, when introduced into the GIT, spontaneously forms dispersion of non-ionic surfactant nanoparticles.

The present invention is applicable to any water-insoluble active pharmaceutical ingredients, or their combination. The compounds are preferably selected but not exclusivity from the group of an immunosuppressive, a fungicide and a virucide compounds. The immunosuppressive group is represented by of N-methylated cyclic undecapeptides, and the macrolide lactones represent namely by tacrolimus or sirolimus. The fungicide group is selected from triazoles, such as ketoconazole, itraconazole, tioconazole; the antiviral group with selective anti-HIV-1 activity represented by non-immunosuppressive cyclosporine analog such as SDZ NIM 811 and HIV inhibitors like stavudine, didanosine and zidovudine and the MDR modifiers represent be non-immunosuppressive N-methylated undecapeptides such as SDZ 033-243, SDZ-PSC-833, and 11-methyl-leucine CsA.

Vitamin A and its synthetically derivates like isotretinoin are also suitable for this Drug delivery system.

The composition of the present invention can be prepared by first dissolving the water-insoluble active ingredient in an organic solvent such as ethanol, propyleneglycol or polyethylene glycol and an amphiphilic co-solvent such as DEGEE, dimethylisosorbide or N-methyl-2-pyrrolidone, to form a solution.

Any suitable water-miscible organic solvent can be used in the present invention. Selection of a suitable organic solvent will depend in part upon the solubility of the active material in the solvent, the degree to which the solvent is miscible in water, and the tolerability of the solvent. The solvent should be physiologically acceptable. Examples of solvents that may be used in the present invention include, but are not limited to, various alcohols such as ethanol, glycols, glycerin, propylene glycol, and various polyethylene glycols and dimethyl isosorbide (DMI).

The hydrophobic and hydrophilic non-ionic surfactants are mixed together to form a homogenous mixture, the mixture maybe heated if necessary. Non-ionic surfactants are selected for their hydrophilic-lipophilic balance (HLB). The HLB is not a universal property, because it is based exclusively on the weight-percent of polyoxyethylene or polyol in the surfactant molecule while disregarding its molecular weight, the chemical nature of its hydrophilic and lipophilic moieties, and the structural features of the latter. Using HLB values as a rough guide, hydrophilic surfactants are considered those compounds having an HLB value greater than 10 particularly from 12 to 17. Similarly, hydrophobic surfactants are compounds having an HLB value less than 10.

The hydrophobic non-ionic surfactant is more soluble in oil than in water, (having a low HLB). Transesterified ethoxylated vegetable oils are particularly suitable.

Examples of transesterified ethoxylated vegetable oils are obtained from corn oil and having an acid number of less than about 2, a saponification number of 155 to 175, an HLB value of 3 to 4, and an iodine number of 90 to 110 or from kernel oil and having an acid number of about 2, a saponification number of 145 to 175, an iodine number of 60 to 90 and an HLB of 4).

The hydrophilic non-ionic surfactant is more soluble in water than in oil (having HLB higher than 10). Examples are reaction products of a natural or polyethoxylated castor oil and ethylene oxide. The ethoxylated castor oil may have an ethylene oxide content of 25 to 100 moles ethylene oxide per molecule, preferably 35 to 60 moles ethylene oxide per molecule. The natural or polyethoxylated castor oil may be reacted with ethylene oxide in a molar ratio of from about 1:35 to about 1:60, with optional removal of the polyethoxylated component from the products.

The polyethoxylated castor oils having a saponification number of about 50 to 60, an acid number less than about 1, a water content less than about 2%, an $n_D^{60}$ of about 1.453 to 1.457 and an HLB of about 12 to 16 are especially suitable.

Also suitable are polyethoxylated castor oils with a molecular weight of about 1630, a saponification number of about 65 to 70, an acid number of about 2, an iodine number of about 28 to 32, an HLB of 16 and an $n_D^{25}$ of about 1.471.

Finally, the products corresponding to a saponification number of about 40 to 50, an acid number less than about 1, an iodine number of less than about 1, a water content of about 4.5 to 5.5%, an $n_D^{25}$ of about 1.453 to 1.457 and an HLB of about 15 to 17 may also be used.

The preferred non-ionic surfactant mixture, according to the present invention, comprise one or more of transesterified ethoxylated vegetable oils combined with one or more polyethoxylated castor oils.

The formulation according to present invention is prepared when the non-ionic surfactant mixture is thoroughly mixed with the solution of the active ingredient in the water-miscible organic solvent/co-solvent. We have found that the formulation of the present invention when diluted with aqueous media or gastric fluids forms dispersion of non-ionic surfactant nanoparticles, preferably below 50 nm as measured by the method described in Pharmacopea Forum—2001, vol 27 (4) page 2724.

One advantage of the preferred embodiments of this invention is that the formulation containing high levels of water-insoluble active pharmaceutical ingredient dissolved in the water miscible solvent/co-solvent, can be diluted with water to produce a thermodynamically stable dispersion of non-ionic surfactant nanoparticles. We have found that such nanoparticles have no tendency to phase separate across a broad range of temperatures at a wide range of water hardness and a wide range of pH.

We have therefore discovered that water insoluble active ingredients particularly pharmaceutical ingredients dissolved in a water-miscible solvent and an amphiphilic co-solvent, can form desirable delivery systems when used with the combination of hydrophilic and hydrophobic non-ionic surfactants.

The preferred embodiments of the invention have the advantage of enabling a water insoluble active pharmaceutical ingredient to be solubilised and transported through the aqueous environmental of the GIT as a dispersion of non-ionic surfactant nanoparticles. The water insoluble ingredient may be present in the system in an amount in the range of 0.001 wt % to 15 wt %, preferably 0.01 wt % to 10 wt %.

Other excipients or additives may be added to the formulation to enhance the efficacy of the active ingredient, to reduce the side effects and/or toxic effects, to prolong the duration of the active ingredient in the systemic circulation. Additional ingredients may also be added to the formulation which enhance the stability of the active pharmaceutical ingredient or formulation, such as anti-oxidants. Still other ingredients may be added to the formulation, such as colourings, flavourings, sweeteners and the like to enhance the receptivity and compliance by patients or other users of the formulations.

The formulation of the present invention is primary intended for oral application of pharmaceuticals, e.g. as a solution, soft gelatin and hard gelatin capsule, however, the system could be used for topically administered compositions, for example in a form of cream, paste, lotion, gel etc.

EXAMPLES

The present invention will now be illustrated by the following examples. It is understood, however, that such examples are provided for illustration only, and the invention is not intended to be limited by the examples. The formulation based on the system employed in the examples can be formed by any suitable method known in the art. In the examples the formulation was mixed with water at a ratio of 1:50 formulation:water to generate the system and measure the particle size formed in water. The particle size was measured by the method described in Pharmacopea Forum—2001 vol 27 (4) page 2724.

The effect of the various components on the average particle size of the formulation when mixed with water is summarized in Example 1 and 2.

Example 1

10% Tioconazole is dissolved in ethanol with stirring at room temperature and mixed with different combinations of according to Table 1. As evident from the table the particles with a smallest Z-average were obtained when the mixture of 10% ethanol, 10% DEGEE, 31.9% Polyethylene glycol oleate (PEG-Oleate), and 38% polyethoxylatedpolyethoxylated castor oil were used. Omitting polyethoxylatedpolyethoxylated castor oil resulted in formation of emulsion with particle size of 450 nm. Omitting DEGEE resulted in 10% increase of particle Z-average (compare with the complete formulation containing DEGEE, PEG Oleate polyethoxylated castor oil).

TABLE 1

| | Triazol - Tioconazole | | | |
|---|---|---|---|---|
| Sample ID | DEGEE (% w/w) | PEG Oleate (% w/w) | Polyethoxylated castor oil (% w/w) | Z-average (nm) |
| A | — | 35.0 | 35.0 | 46 |
| B | 35.0 | — | 35.0 | not measurable |
| C | 35.0 | 35.0 | — | 450 |
| D | 10.0 | 31.9 | 38.0 | 41.5 |

Example 2

10% of the cyclic N-methyl undecapeptides, namely CsA, CsC and CsG were solubilized in ethanol followed by mixing with the DEGEE, PEG Oleate and Polyethoxylated castor oil used in Example 1. As shown in Table 2, the formula behaved similarly to tioconazol, formulation providing particle Z-average of 37.5 nm.

Particle size results were the same for all three cyclic undecapeptides. Besides the impact on particle size, the presence of DEGEE significantly improved technological parameters of the formulation, especially its tolerance to water during the soft gelatine capsule production.

TABLE 2

| | | | Cyclic N-methylated undecapeptides | |
|---|---|---|---|---|
| Sample ID | DEGEE (% w/w) | PEG Oleate (% w/w) | Polyethoxylated castor oil (% w/w) | Z-average (nm) |
| F | — | 40.0 | 40.0 | 42.8 |
| G | 40.0 | — | 40.0 | 183.1 |
| H | 40.0 | 40.0 | — | 918.9 |
| I | 10.0 | 31.9 | 38.0 | 37.5 |

Example 3

0.5% tacrolimus API was dissolved in ethanol and mixed with DEGEE, PEG Oleate and Polyethoxylated castor oil used in Example 1 according to Table 3, providing particles of Z-average of 32 nm.

TABLE 3

| | | | Tacrolimus | |
|---|---|---|---|---|
| Sample ID | DEGEE (% w/w) | PEG Oleate (% w/w) | Polyethoxylated castor oil (% w/w) | Z-average (nm) |
| J | 15.5 | 31.9 | 38.0 | 32.0 |

Example 4

0.1% sirolimus was dissolved in ethanol and mixed with DEGEE, PEG Oleate and Polyethoxylated castor oil used in Example 1 according to Table 4, providing the particles of Z-average of 35 nm.

TABLE 4

| | | | Sirolimus | |
|---|---|---|---|---|
| Sample ID | DEGEE (% w/w) | PEG Oleate (% w/w) | Polyethoxylated castor oil (% w/w) | Z-average (nm) |
| E | 15.0 | 31.9 | 38.0 | 35.0 |

The invention claimed is:

1. A composition for delivering an active pharmaceutical ingredient comprising:
   i) a water insoluble active pharmaceutical ingredient comprising one or any combination of tacrolimus, sirolimus, ketoconazole, itraconazole, tioconazole and a cyclic N-methyl undecapeptide;
   ii) a water miscible solvent(s) comprising ethanol, propylene glycol, or a combination thereof;
   iii) an amphiphilic co-solvent(s) comprising diethylene glycol monoethylether, 1,3-dimethylisosorbide or a combination thereof;
   iv) at least one hydrophilic and one hydrophobic non-ionic surfactant comprising one polyethoxylated castor oil or a combination of polyethoxylated castor oils having a hydrophilic-lipophilic balance value higher than 12 and lower than 16 as the hydrophilic surfactant(s); and PEG-6 oleate as the hydrophobic surfactant;
   wherein the composition is free of triglycerides.

2. The composition according to claim 1 wherein said water-insoluble active pharmaceutical ingredient(s) are present in the amount of 0.01% wt to 10% wt.

3. The composition according to claim 1 wherein the mixture of hydrophilic and hydrophobic surfactants is present in amount from 55 to 95% by weight based on the total weight of the composition.

4. The composition of claim 1 in which the delivery is oral.

5. The composition of claim 4 in which the delivery is as a solution or a capsule.

6. The composition of claim 1 in which the delivery is topical.

7. The composition of claim 6 in which the delivery is in a form of a cream, paste, lotion or gel.

8. The composition according to claim 1 wherein said water-insoluble active pharmaceutical ingredient(s) are present in the amount of 0.001 wt % to 15 wt %.

9. The composition according to claim 1 in which when in contact to aqueous media forms a transparent dispersion of nanoparticles with size below 100 nm.

10. The composition according to claim 1 in which the water insoluble compound includes active pharmaceutical ingredients with water solubility less than 30 mg/ml.

11. The composition according to claim 1 which is mixed with water at a ratio of 1:50.

12. The composition according to claim 1 including colourings, flavourings, and/or sweeteners.

13. The composition according to claim 2 including 10% tioconazole.

14. The composition according to claim 2 including 10% cyclic N-methyl undecapeptides.

15. The composition according to claim 2 including 0.5% tacrolimus.

16. The composition according to claim 2 including 0.1% sirolimus.

17. The composition according to claim 2, wherein the water miscible solvent comprises 10% ethanol.

18. The composition according to claim 2, wherein the amphiphilic co-solvent comprises 10% to 40% diethylenglycol monoethylether.

19. The composition according to claim 2 including 35% to 40% polyethoxylated castor oils.

20. The composition according to claim 1 including about 31% to 40% PEG Oleate.

* * * * *